(12) United States Patent
Dupont

(10) Patent No.: US 11,975,293 B2
(45) Date of Patent: May 7, 2024

(54) TANGENTIAL FLOW FILTRATION DEVICE FOR PERFUSION APPLICATIONS

(71) Applicant: EMD Millipore Corporation, Burlington, MA (US)

(72) Inventor: Alison Dupont, Lyndeborough, NH (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 17/655,093

(22) Filed: Mar. 16, 2022

(65) Prior Publication Data

US 2022/0203303 A1 Jun. 30, 2022

Related U.S. Application Data

(63) Continuation of application No. 16/607,468, filed as application No. PCT/US2018/034709 on May 25, 2018, now abandoned.

(Continued)

(51) Int. Cl.
*B01D 63/10* (2006.01)
*B01D 61/18* (2006.01)
(Continued)

(52) U.S. Cl.
CPC .......... *B01D 63/103* (2013.01); *C12M 29/10* (2013.01); *B01D 61/18* (2013.01); *B01D 65/02* (2013.01);
(Continued)

(58) Field of Classification Search
CPC ...... B01D 63/103; B01D 61/18; B01D 65/02; B01D 65/08; B01D 2311/04;
(Continued)

(56) References Cited

U.S. PATENT DOCUMENTS 5,225,080 A 7/1993 Karbachsch et al.
6,544,425 B2 4/2003 Miller
(Continued)

FOREIGN PATENT DOCUMENTS

CN 106132517 A 11/2016
JP 8-270595 A 10/1996
(Continued)

OTHER PUBLICATIONS

Office Action received for Japanese Patent Application No. 2019-566212 dated Jan. 10, 2023, 4 Pages (2 Pages of English translation & 2 Pages of official copy).
(Continued)

*Primary Examiner* — Pranav N Patel
(74) *Attorney, Agent, or Firm* — EMD Millipore Corporation

(57) ABSTRACT

Filter elements for perfusion systems and methods are provided. A filter element sheet includes a microporous membrane having a mean pore size of at least about 0.65 μm and a feed spacer comprising woven fibers and having an open area of at least about 35%. The filter element sheet can be arranged within a filter element, for example, in a spiral-wound format or in a cassette format. A perfusion system includes at least one filter element and a pump configured to control flow of a liquid feed through the at least one filter element.

18 Claims, 15 Drawing Sheets

Related U.S. Application Data

(60) Provisional application No. 62/513,793, filed on Jun. 1, 2017.

(51) Int. Cl.
*C12M 1/00* (2006.01)
*B01D 65/02* (2006.01)
*B01D 65/08* (2006.01)

(52) U.S. Cl.
CPC .......... *B01D 65/08* (2013.01); *B01D 2311/04* (2013.01); *B01D 2311/06* (2013.01); *B01D 2313/143* (2013.01); *B01D 2315/10* (2013.01); *C12M 29/04* (2013.01)

(58) Field of Classification Search
CPC .......... B01D 2311/06; B01D 2313/143; B01D 2315/10; B01D 63/082; B01D 2311/25; B01D 63/10; B01D 2313/243; B01D 2325/02; C12M 29/10; C12M 29/04; C12M 47/10; C12M 33/14; C07K 1/34
See application file for complete search history.

(56) References Cited

U.S. PATENT DOCUMENTS

| | | | | |
|---|---|---|---|---|
| 2011/0212493 | A1* | 9/2011 | Hirschel | C12M 29/10 435/235.1 |
| 2013/0345402 | A1* | 12/2013 | Vogel | C07K 1/145 530/383 |
| 2014/0093952 | A1 | 4/2014 | Serway | |
| 2015/0158907 | A1 | 6/2015 | Zhou et al. | |
| 2015/0247114 | A1* | 9/2015 | Gebauer | F04B 43/0081 435/243 |
| 2015/0375173 | A1 | 12/2015 | Steen | |
| 2016/0068565 | A1 | 3/2016 | Shibano et al. | |
| 2016/0222337 | A1 | 8/2016 | Serway | |
| 2018/0257042 | A1* | 9/2018 | Hester | B01D 71/40 |

FOREIGN PATENT DOCUMENTS

| | | |
|---|---|---|
| JP | 2002-180986 A | 6/2002 |
| JP | 2016-54686 A | 4/2016 |
| JP | 2016-530087 A | 9/2016 |
| WO | 99/07458 A1 | 2/1999 |
| WO | 2014/051503 A1 | 4/2014 |
| WO | 2015/200691 A1 | 12/2015 |
| WO | 2016/049281 A1 | 3/2016 |
| WO | 2018/222550 A1 | 12/2018 |

OTHER PUBLICATIONS

Examination Search Report received for Canada Patent Application No. 3,060,705, dated Oct. 5, 2021, 4 pages.
International Search Report and Written Opinion for International Application No. PCT/US2018/034709, dated Sep. 24, 2018, 9 pages.
Non Final Office Action Received for U.S. Appl. No. 16/607,468, dated Mar. 24, 2022, 13 Pages.
Office Action received for Chinese Patent Application No. 201880032379.0, dated Oct. 31, 2022, 14 Pages (6 Pages of English Translation & 8 Pages of Official Copy).
Communication pursuant to Article 94(3) EPC received for European Patent Application No. 18731317.6 dated Mar. 31, 2023, 5 Pages.
Office Action received for Chinese Patent Application No. 201880032379.0 dated Aug. 2, 2023, 4 Pages (1 Page of English translation & 3 Pages of official copy).
Office Action received for Japanese Patent Application No. 2021-188462 dated Jul. 11, 2023, 12 Pages (6 Pages of English Translation & 6 Pages of Official Copy).

* cited by examiner

| Screen | Experimental Results ||||| Model Results ||||
|---|---|---|---|---|---|---|---|---|
| | Feed Flow (ml/min) | Ret. Flow (ml/min) | Perm Flow (ml/min) | Feed Press (psi) | Ret Press (psi) | Perm Press (psi) | Calculated Feed Pressure | Error (%) |
| D3 | 11 | 10 | 1 | 4.51 | 4.22 | 3.2 | 4.63 | 2.6 |
| | 30.5 | 30 | 0.5 | 4.51 | 3.93 | 3.49 | 4.61 | 2.2 |
| | 50.7 | 50 | 0.7 | 4.66 | 3.35 | 3.06 | 4.689 | 0.6 |
| | 102.4 | 100 | 2.4 | 9.46 | 6.26 | 3.93 | 9.462 | 0.02 |
| D | 11.1 | 10 | 1.1 | 4.51 | 4.08 | 3.2 | 4.53 | 0.4 |
| | 61.3 | 60 | 1.3 | 6.4 | 3.93 | 3.06 | 6.25 | -2.3 |
| | 105.9 | 100 | 5.9 | 10.19 | 5.53 | 2.91 | 10.518 | 3.2 |

FIG. 6

TANGENTIAL FLOW FILTRATION DEVICE FOR PERFUSION APPLICATIONS

RELATED APPLICATION(S)

This application is a continuation of U.S. application Ser. No. 16/607,468, filed Oct. 23, 2019, which is a U.S. National Stage application of International Application No. PCT/US2018/034709, filed May 25, 2018, which claims the benefit of U.S. Provisional Application No. 62/513,793, filed on Jun. 1, 2017. The entire teachings of the above applications are incorporated herein by reference.

BACKGROUND

Monoclonal antibodies (mAbs) are used as therapeutic agents for a variety of indications, including, for example, cancer, transplant rejections, and cardiovascular disease. Various biopharmaceutical manufacturing techniques exist to produce and harvest mAbs from host cells, including, for example, fed-batch processes and perfusion processes. In fed-batch bioreactor systems, cells are cultured in batches over a set period of time, for example, over about seven to about twenty-one days, after which point media nutrients have been consumed by the host cells and waste products have accumulated. Following the cell culture period, the batch undergoes a harvesting step in which the protein of interest (e.g., a product, such as a monoclonal antibody, or mAb) is separated from the cell mass. In contrast with fed-batch systems, perfusion bioreactors culture cells over longer periods of time, for example, over several weeks or months, while continuously feeding cells with fresh media, removing spent media, and harvesting product. Perfusion systems offer several advantages over fed-batch systems. For example, as product is harvested and purified on a continuous basis, before the proteins of interest are exposed to high levels of waste, product degradation is reduced in perfusion systems. In addition, a perfusion bioreactor can produce a similar product yield as a fed-batch bioreactor while occupying a significantly smaller space. Perfusion is becoming a preferred manufacturing technique in the biopharmaceutical industry due to its advantages over batch-fed processes. However, perfusion processes rely on a high density of host cells being maintained throughout each production process, and continuous harvesting, which involves several iterations of filtration, and can cause physical damage to the host cells.

SUMMARY OF THE INVENTION

Conventional perfusion systems and processes use filter elements having open feed channels to avoid obstructions that could cause damage to host cells. However, filter elements used in such conventional systems and processes have relatively short lifespans, exhibiting significantly reduced sieving at low harvest throughputs due to membrane fouling. Filter elements for perfusion systems and methods are provided that exhibit improved sieving and throughput of mAbs as compared with existing open-channel and hollow fiber devices.

In an embodiment, the invention encompasses a filter element sheet that includes a microporous membrane having a mean pore size of at least about 0.65 μm and a feed spacer comprising woven fibers and having an open area of at least about 35%.

Feed spacers comprising woven fibers and having an open area of at least about 35% can provide for low shear rates within a feed channel of a filter element, such that host cells are not damaged during filtration. The feed spacer can have an open area of, for example, about 35% to about 55%, and can comprise fibers having an average fiber diameter of at least about 270 μm, for example, about 300 μm to about 500 μm. The pore size of a feed spacer can be, for example, about 0.8 μm to about 10 μm, or about 1.0 μm to about 5 μm. A fiber density of the feed spacer can be of about 6 fibers/cm to about 13 fibers/cm. The fibers of the feed spacer can be woven in a two-over-one twill pattern or a one-over-one weave pattern.

In another embodiment, the invention provides for a filter element that includes at least one filter element sheet as described herein. The filter element can be a spiral-wound filter element or a cassette filter element.

In a further embodiment, the invention encompasses a perfusion system that includes at least one filter element as described herein and a pump configured to control flow of a liquid feed through the at least one filter element.

Such perfusion systems can be configured to be operated in, for example, a tangential flow filtration (TFF) mode, a recirculation mode, and/or an alternating flow mode. The pump can be, for example, a magnetic levitation pump, a peristaltic pump, or a diaphragm pump.

In yet another embodiment, the invention relates to a perfusion process that includes passing a liquid feed through a feed channel of at least one filter element and separating the liquid feed into permeate and retentate by tangential flow filtration (TFF) in the filter element. The filter element includes a microfiltration membrane and a woven feed spacer located within the feed channel. Cells and a target protein can be present in the liquid feed.

In further embodiments, perfusion processes of the present invention can also include recovering the target protein in the permeate and/or retaining the cells in the retentate. In some embodiments, at least a portion of the retentate can be recirculated through the at least one filter element. Additionally, or alternatively, flow of liquid through the at least one filter element can be alternated for self-cleaning of the filter element. The perfusion process can also include supplying a volume of fresh media to the retentate and returning the retentate and fresh media to a bioreactor. The perfusion process can be run on a continuous basis, with the retentate of an initial perfusion run being the liquid feed of a subsequent perfusion run.

In another embodiment, the invention provides for a perfusion process for harvesting target proteins from a liquid feed containing host cells. The process includes delivering a liquid feed containing target proteins and host cells to a feed channel of at least one filter element and separating the target proteins from the host cells in the at least one filter element. The at least one filter element includes a microfiltration membrane and a woven feed spacer located within the feed channel. The target proteins can be, for example, monoclonal antibodies, which can be separated from the host cells by TFF and recovered from the at least one filter element. The perfusion process can further include recovering the host cells from the at least one filter element, supplying a volume of fresh media to the recovered host cells, and returning the recovered host cells to a bioreactor. The perfusion process can be run on a continuous basis, with the recovered host cells of an initial perfusion run being the liquid feed of a subsequent perfusion run.

Perfusion processes of the present invention can provide for improved sieving over conventional perfusion processes involving open-channel filtration devices. In some embodiments, at least about 80%, at least about 90%, or at least about 95% of the target proteins can be recovered from the liquid feed at a harvest throughput of at least about 500 L/m² of the filter element. In other embodiments, at least about 80%, at least about 90%, or at least about 95% of the target proteins can be recovered from the liquid feed at a harvest throughput of at least about 1000 L/m² of the filter element.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 6 is a table of model results and experimental results for woven-fiber feed spacers.

DETAILED DESCRIPTION OF THE INVENTION

Definitions

Figure 1:
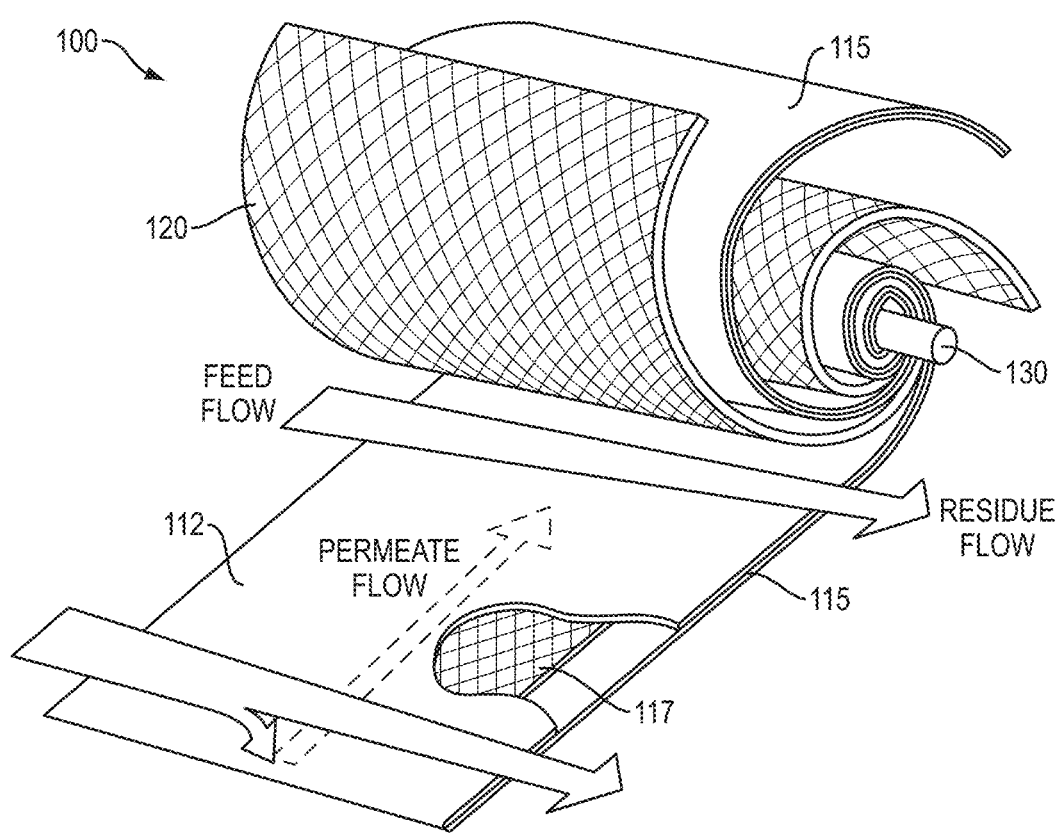
FIG. 1 is a diagram illustrating an example of a spiral-wound filter element.

Unless defined otherwise, all technical and scientific terms used herein have the same meaning as commonly understood by one of ordinary skill in the art to which this invention pertains.

As used herein, the singular forms "a", "an," and "the" include plural unless the context clearly dictates otherwise.

The expression "spiral-wound filter element" refers to a filtration membrane that is spirally wound about a core. A spiral-wound filter element may be contained within a housing and may alternately be referred to as a spiral-wound filter module.

"Pressure drop" refers to the drop in pressure (e.g., psid) within a feed channel over the length of the filter element.

"Flux" is the area-normalized flow rate.

"Permeate flux" is the area normalized flow rate of permeate in a permeate channel (e.g., Liters/hr/m2, lmh).

"Cross-flow flux" is the area normalized average flow rate of retentate in a feed channel (e.g., Liters/min/m2, LMM).

"Cross-flow" is the retentate flow rate between inlet and outlet of the feed channel in a filter or a series of filters. Unless otherwise stated, "cross-flow" refers to an average cross-flow.

The term "shear" refers to a strain in the structure of a substance that is produced by pressure.

The term "shear rate" refers to the rate at which a progressive shearing deformation is applied (e.g., $s^{-1}$).

The terms "feed," "feed sample" and "feed stream" refer to the solution being introduced into a filtration module for separation.

The term "separation" generally refers to the act of separating the feed sample into two streams, a permeate stream and a retentate stream.

The terms "permeate" and "permeate stream" refer to that portion of the feed that has permeated through the membrane.

The terms "retentate" and "retentate stream" refer to the portion of the solution that has been retained by the membrane, and the retentate is the stream enriched in a retained species.

"Feed channel" refers to a conduit in a filtration assembly, module or element for a feed.

"Permeate channel" refers to a conduit in a filtration assembly, module, or element for a permeate.

The expression "flow path" refers to a channel comprising a filtration membrane (e.g., ultrafiltration membrane, microfiltration membrane) through which the solution being filtered passes (e.g., in a tangential flow mode). The flow path can have any topology which supports tangential flow (e.g., straight, coiled, arranged in zigzag fashion). A flow path can be open, as in an example of channels formed by hollow fiber membranes, or have one or more flow obstructions, as in the case, for example, of rectangular channels formed by flat-sheet membranes spaced apart by woven or non-woven spacers.

"TFF assembly," "TFF system" and "TFF apparatus" are used interchangeably herein to refer to a tangential flow filtration system that is configured for operation in a single-pass mode and/or a recirculation mode (e.g., full or partial recirculation) and/or alternating flow mode.

"Single leaf" spirals are spiral-wound filter elements that can be formed with one continuous feed channel. They are generally made with one sheet of membrane.

"Multi-leaf" spirals are spiral-wound filter elements that have multiple feed channels. They are generally made with more than 1 sheet of membrane; but can be made with 1 membrane sheet also.

A "cassette holder" refers to a compression assembly for one or more cassettes. Typically, when a cassette holder contains more than one cassette, the cassettes are configured for parallel processing, although, in some embodiments, the cassettes can be configured for serial processing.

A "cassette" refers to a cartridge or flat plate module comprising filtration (e.g., ultrafiltration or microfiltration) membrane sheet(s) suitable for TFF processes.

"Filtration membrane" refers to a selectively permeable membrane capable of use in a filtration system, such as a TFF system.

The term "microfiltration membranes" and "MF membranes" are used herein to refer to membranes that have pore sizes in the range between about 0.1 micrometers to about 10 micrometers.

"Fluidly connected" refers to a plurality of spiral-wound membrane TFF modules that are connected to one another by one or more conduits for a liquid, such as, a feed channel, retentate channel and/or permeate channel.

"Product" refers to a target compound. Typically, a product will be a biomolecule (e.g., protein) of interest, such as a monoclonal antibody (mAb).

"Processing" refers to the act of filtering (e.g., by TFF) a feed containing a product of interest and subsequently recovering the product (e.g., in a purified form). The product can be recovered from the filtration system (e.g., a TFF assembly) in either the retentate stream or permeate stream depending on the product's size and the pore size of the filtration membrane.

The expressions "parallel processing", "processing in parallel", "parallel operation" and "operation in parallel" refer to processing a product in a TFF assembly that contains a plurality of processing units that are fluidly connected by distributing the feed directly from a feed channel or manifold to each of the processing units in the assembly.

The expressions "serial processing", "processing in series", "serial operation" and "operation in series" refer to processing a product in a TFF assembly that contains a plurality of processing units that are fluidly connected by distributing the feed directly from the feed channel to only the first processing unit in the assembly. In serial processing, each of the other, subsequent processing units in the assembly receives its feed from the retentate line of the preceding processing unit (e.g., the retentate from a first processing unit serves as the feed for a second, adjacent processing unit).

A description of example embodiments of the invention follows.

Tangential Flow Filtration in Perfusion Systems

Perfusion systems and methods, in contrast with fed-batch systems, involve continuous filtration of cell culture media. During filtration, target proteins, such as mAbs, and optionally other soluble components, such as cellular waste products (e.g., lactic acid and ammonia), are removed from the cell culture media. Perfusion systems (alternately referred to as cell-retention systems) present unique challenges over fed-batch systems as the cells contained in a perfusion system pass repeatedly through filtration equipment, which can cause physical damage to the cells and which, in turn, can reduce productivity of the system. It is desirable to minimize cell damage during filtration in perfusion systems so as to retain as many cells as possible for ongoing production of the target protein.

Tangential flow filtration (TFF) is a separation process that uses membranes to separate components in a liquid solution or suspension on the basis of size, molecular weight or other differences. TFF is used in perfusion processes to remove target proteins from cell culture media, while retaining cells within the media. In TFF processes, fluid is pumped tangentially along the membrane surface and particles, molecules, or cells that are too large to pass through the membrane are rejected and returned to a process tank. TFF processes can involve additional passes of the fluid across the membrane (e.g., recirculation) until the process fluid is sufficiently clarified, concentrated or purified. The cross-flow nature of TFF minimizes membrane fouling, thus permitting high volume processing per batch. The membranes are contained within filter elements that can be of a variety of configurations, such as spiral-wound filter elements (FIG. 1) and cassette filter elements (FIG. 2).

Current TFF devices used in perfusion systems include hollow fiber devices and open-channel cassette devices, also referred to as plate-and-frame devices. Examples of currently-available filtration devices for perfusion systems include XCell™ ATF System (Repligen, Waltham, MA) and KrosFlo® Perfusion System (Spectrum Laboratories, Rancho Dominguez, CA), which are hollow fiber devices, and Prostak™ Microfiltration Modules (MilliporeSigma, Billerica, MA), which are cassette devices. These devices contain open feed channels, so as to limit physical damage to cells in the feed stream, and both devices require high cross-flow rates to minimize fouling (i.e., the accumulation of particles along the wall of membrane). Membrane fouling reduces product recovery because the passage of target proteins and waste materials through the membrane (i.e., sieving) is reduced. Eventually, membrane fouling can result in failure of the device, with product no longer being recovered during filtration.

Perfusion Filter Elements with Low-Shear Feed Spacers

Filter elements for perfusion systems are provided that exhibit improved sieving and throughput of mAbs as compared with open-channel devices, while minimizing cell damage during filtration. In particular, perfusion filter element sheets are provided that include a combination of open microporous membrane(s) and low-shear feed spacer(s). The combination of an open membrane (e.g., membranes having a pore size greater than about 0.65 μm, greater than about 1.0 μm, or greater than about 3 μm) with a low-shear feed spacer promotes mixing in the feed channel to minimize fouling while also maintaining shear rates at the membrane and fiber surfaces that are within cell stability limits.

In one embodiment, the invention encompasses a perfusion filter element sheet includes a microporous membrane and a woven-fiber feed spacer. The microporous membrane can have a mean pore size of at least about 0.65 μm (e.g., 0.62 μm, 0.65 μm, 0.67 μm, 0.8 μm), at least about 1.0 μm (e.g., 0.95 μm, 1.0 μm, 1.2 μm), or at least about 3.0 μm (e.g., 2.9 μm, 3.0 μm, 5 μm). The mean pore size can be of about 0.8 μm to about 10 μm (e.g., 0.77 μm, 0.8 μm, 0.9 μm, 2 μm, 4 μm, 6 μm, 8 μm, 10.3 μm), or of about 1.0 μm to about 5 μm (e.g., 0.97 μm, 1.2 μm, 3 μm, 5.3 μm). The mean pore size can be selected to provide for sieving of target proteins and/or waste materials from a cell culture fluid, while retaining cells within the cell culture fluid. Examples of suitable microporous membranes include the membranes listed in Table 1, below.

TABLE 1

Examples of microporous membranes.

| Membrane | Pore Size (μm) | Permeability (ml/min/cm2) | Manufacturer |
| --- | --- | --- | --- |
| Cellulose Acetate | 0.8 | 81.3 | Sterlitech |
| Cellulose Acetate | 1.2 | 180 | Sterlitech |
| Cellulose Acetate | 3 | 500 | Sterlitech |
| Cellulose Acetate | 5 | 375 | Sterlitech |
| Mixed Cellulose Ester | 0.8 | 165 | Sterlitech |
| Mixed Cellulose Ester | 1 | 220 | Sterlitech |
| Mixed Cellulose Ester | 3 | 300 | Sterlitech |
| Mixed Cellulose Ester | 5 | 400 | Sterlitech |

TABLE 1-continued

Examples of microporous membranes.

| Membrane | Pore Size (μm) | Permeability (ml/min/cm2) | Manufacturer |
|---|---|---|---|
| Mixed Cellulose Acetate | 1.2 | 270 | MilliporeSigma |
| Mixed Cellulose Acetate | 3 | 320 | MilliporeSigma |
| Mixed Cellulose Acetate | 5 | 580 | MilliporeSigma |
| Dupore (PVDF) | 1 | >100 | MilliporeSigma |
| Dupore (PVDF) | 1.2 | >100 | MilliporeSigma |
| Dupore (PVDF) | 5 | >208 | MilliporeSigma |
| Nylon | 0.8 | 120 | Sterlitech |
| Nylon | 1.2 | 190 | Sterlitech |
| Polycarbonate | 0.8 | 90 | Sterlitech |
| Polycarbonate | 1 | 130 | Sterlitech |
| Polycarbonate | 2 | 300 | Sterlitech |
| Polycarbonate | 3 | 440 | Sterlitech |
| Polyester | 0.8 | 90 | Sterlitech |
| Polyester | 1 | 130 | Sterlitech |
| Polyester | 2 | 300 | Sterlitech |
| Polyester | 3 | 440 | Sterlitech |
| PES | 0.8 | 117 | Sterlitech |
| PES | 1.2 | 143 | Sterlitech |
| PES | 5 | 186 | Sterlitech |

The feed spacer can include woven fibers that are woven in a two-over-one twill pattern or a one-over-one weave pattern. The feed spacer can have an open area of at least about 35%, or of about 35% to about 55% (e.g., 34.5%, 35%, 36%, 39%, 40%, 50%, 55%, 55.5%). A fiber density of the feed spacer can be of about 6 fibers/cm to about 13 fibers/cm (e.g., 5.5 fibers/cm, 6 fibers/cm, 8 fibers/cm, 10.6 fibers/cm, 12.2 fibers cm, 13.5 fibers/cm). The feed spacer fibers can have a mean fiber diameter of at least about 270 μm (e.g., 265 μm, 270 μm, 275 μm), or of about 300 μm to about 500 μm (e.g., 290 μm, 300 μm, 400 μm, 500 μm, 510 μm).

Examples of suitable feed spacers include D-screens (Propyltex® screens, product no. 05-500/36, Sefar, QC, Canada) having a two-over-one twill pattern, an open area of 36%, a fiber density of 12.2 fibers/cm, fiber diameter of 340 μm, and a thickness of 610 μm, and D3-screens (Propyltex® screens, product no. 05-590/39, Sefar, QC, Canada) having a two-over-one twill pattern, an open area of 39%, a fiber density of 10.6 fibers/cm, fiber diameter of 360 μm, and a thickness of 645 μm. Another example of a suitable feed spacer is an E screen (PETER® screen, product no. 07-840/46, Sefar, QC, Canada) having a one-over-one weave pattern, an open area of 46%, a fiber density of 8 fibers/cm, fiber diameter of 400 microns, and a thickness of 785 microns.

In another embodiment, the invention provides a filter element that includes a filtration sheet as described above. The filter element can be a spiral-wound filter element or a cassette filter element.

Figure 2:
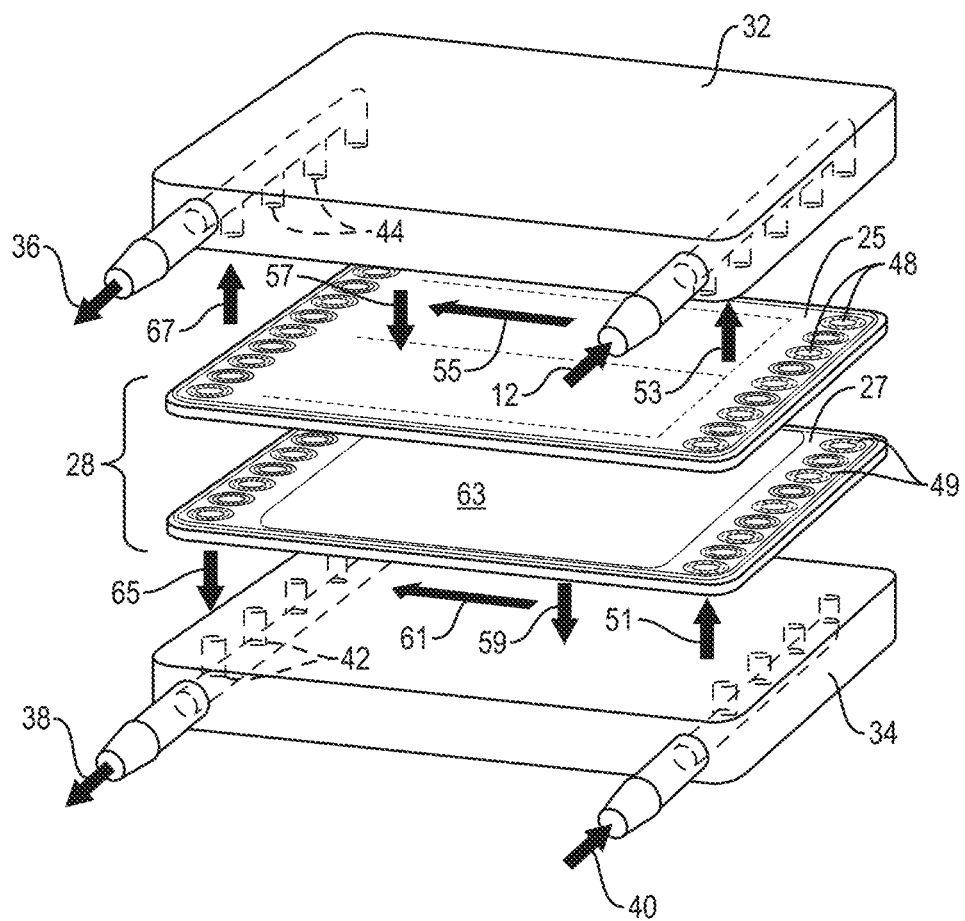
FIG. 2 is an exploded view of an example of a cassette filter element.

An example of a spiral-wound filter element 100 is illustrated in FIG. 1, with arrows indicating feed flow direction and arrows indicating permeate flow within a membrane envelope 115. The membrane envelope 115 includes a membrane 112 folded over an optional permeate spacer 117. One or more membrane envelopes 115 can be included in a spiral-wound filter element. Membrane envelope(s) 115 are in planar contact with the outer surfaces of feed spacer(s) 120. The membrane envelope(s) 115 and feed spacer(s) 120 are wound about a perforated permeate collection pipe 130.

In a perfusion process, cell culture media is introduced to a feed-side of the membrane 112. As the liquid feed (e.g., the cell culture media) travels across the surface of the membrane 112 and through and around the feed spacer 120, it is separated into permeate and retentate. Specifically, target proteins pass through the membrane 112 and are recovered from the permeate exiting the filter through collection tube 130. Cells are retained and are recovered from the retentate exiting the filter. The cell culture media in the retentate can then be returned to a bioreactor, and the target proteins contained in the permeate can be collected in a separate vessel for further processing.

An example of a cassette filter 20 is illustrated in FIG. 2. The cassette filter 20 includes a cassette filter element 28 having at least one feed plate 25 and at least one membrane plate 27. The feed plate 25 can include or be partially formed of woven fiber feed-spacer. The membrane plate 27 includes a membrane 63. The filter element 28 is positioned between a manifold 32 and a manifold 34. Manifold 32 includes a feed inlet 12 and a retentate outlet 36. Manifold 34 includes a permeate outlet 38 and a feed inlet 40. Holes 48, 49 located on the feed and membrane plates 25, 27 are sealed in a configuration such that liquid feed entering the filter 20 (e.g., through feed inlets 12, 40) travels in a path represented sequentially by arrows 51, 53, 55, and 57 and separates into permeate and retentate. Retentate, which does not pass through membrane 63, travels to retentate conduits 44 and exits the filter through retentate outlet 36 (as shown by arrow 67). Permeate, which passes through membrane 63 then travels in a path represented sequentially by arrows 59, 61, and 65, traveling through permeate conduit 42 and exiting the filter through permeate outlet 38.

Filter elements of the present invention (e.g., spiral-wound filter elements or cassette filter elements), provide several advantages over existing hollow fiber and cassette devices used in perfusion systems. Conventional filtration devices for the purification of monoclonal antibodies typically include membranes having a mean pore size of about 0.2 μm to about 0.5 μm. In contrast, microporous membranes included in embodiments of the present invention can be considered "open" microporous membranes, having a mean pore size of at least about 0.65 μm, for example, at least about 1.0 μm, or at least about 3 μm. The results of Examples 3 and 5 herein demonstrate that open microporous membranes provide improved sieving performance over conventional filtration devices that have membranes with pore sizes of 0.2 μm or 0.5 μm. As membrane pore size increases, it is likely that more cellular debris passes through the membrane. As understood by the inventor of the present invention, and without adhering to any particular theory, it is believed that cellular debris fragments interact with proteins and DNA through electrostatic and hydrophobic interaction to form a gel like layer on membrane surfaces in conventional perfusion filtration devices. Such interaction increases fouling and reduces sieving in devices having "tighter" membranes (e.g., membranes having pore sizes of 0.2 μm or 0.5 μm). Additionally, feed screens are not included in existing perfusion devices as they are believed to impose unacceptable shear stresses on cells travelling through the filter, which is undesirable in cell-retention systems.

Figure 7:
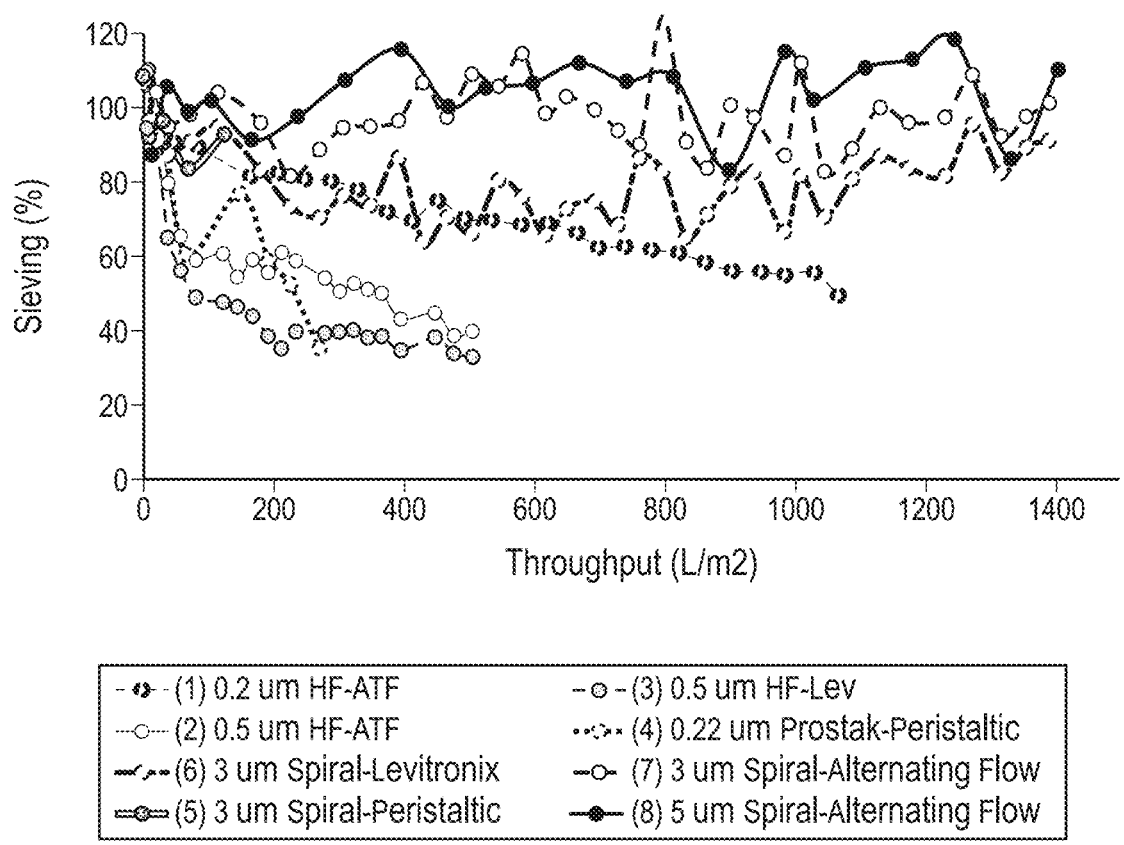
FIG. 7 is a graph of experimental results of sieving versus harvest throughput of tangential flow filtration devices.

The sieving performance of conventional filtration devices decreases sharply during operation, with sieving reduced to approximately 40% after a harvest throughput of only 200 L/m$^2$ or 400 L/m$^2$, as shown in FIG. 7. As further described in Examples 3 and 5, example embodiments of the present invention, which have open microporous membranes and woven-fiber feed spacer sheets, are able to achieve about 100% sieving over a harvest throughput of at least about 500 L/m$^2$ (e.g., with a membrane pore size of about 1 μm) or at least about 1000 L/m² (e.g., with a membrane pore size of about 3 μm or about 5 μm). As such, examples of filter elements of the present invention demonstrate improved sieving over longer periods of operation, as compared with existing perfusion filters. Additionally, the results of Examples 1-4 herein demonstrate that woven fiber spacer sheets having an open area of at least about 35% can promote sufficient turbulence in a feed channel to reduce fouling while resulting in acceptable shear rates for cells passing through the feed channel.

Perfusion Systems

Filter elements of the present invention can be included a perfusion system. The perfusion system can include a TFF system having one or more than one spiral-wound filter element or cassette filter element described herein. In systems having more than one filter element, the filter elements can be fluidly connected in series or in parallel, or both.

Figure 3:
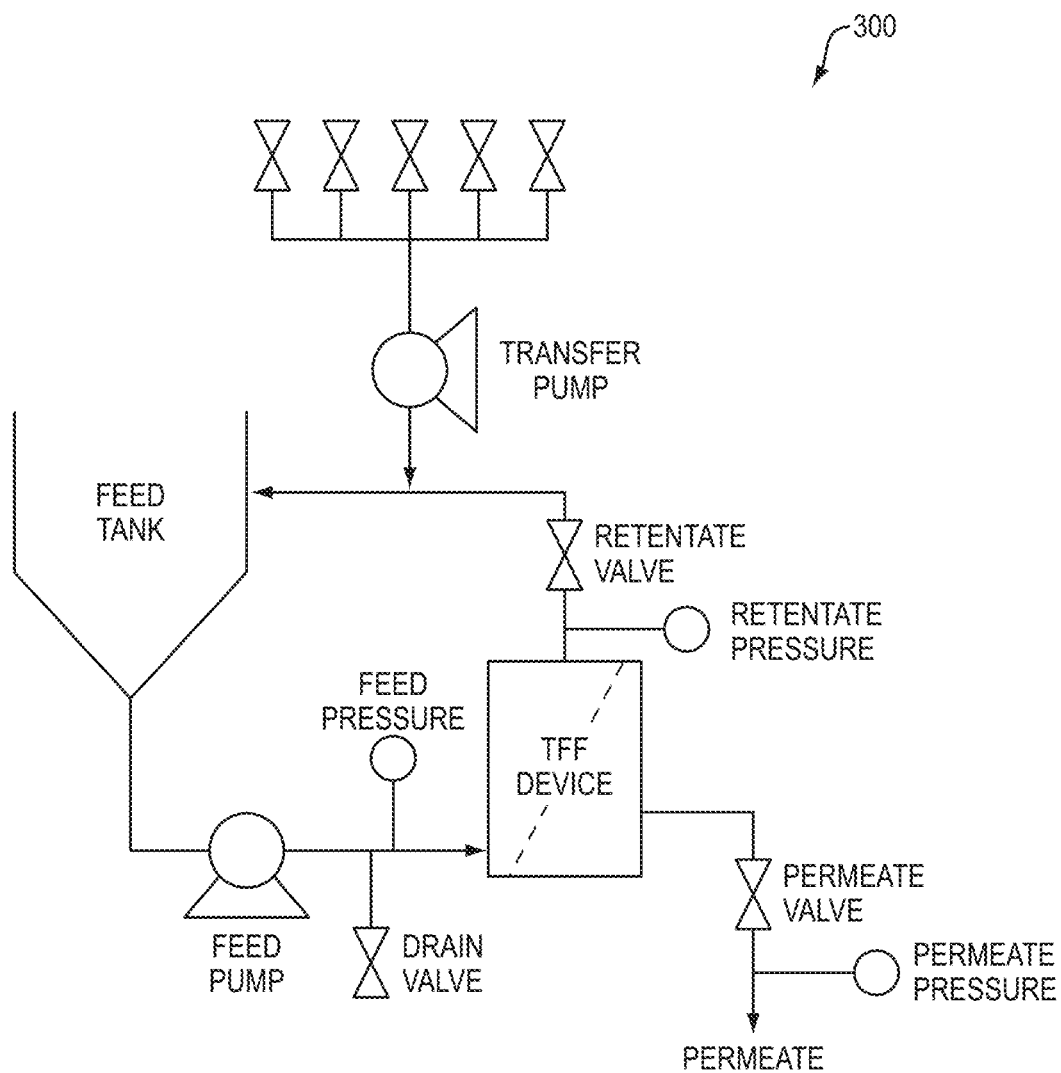
FIG. 3 is a schematic illustrating an example of a TFF system.

An example TFF system 300 is shown in FIG. 3. Pressurized feed from a feed tank is connected to the feed port of the spiral-wound filter module or manifold of the cassette filter. Feed flows through the membrane lined feed channel of the TFF device(s) under an applied trans-channel pressure drop, typically achieved by pressurizing the feed using a pump. Some of the solvent from the feed stream flows through the face of the membrane into the permeate channel and carries with it a portion of the permeable species (e.g., target protein, waste products). The remaining concentrated feed stream flows out of the module or manifold through the retentate port. The permeate flowing from the module's permeate port is directed to a location that is dependent on the process, where it is either collected (e.g., as with target protein) or discarded (e.g., as with waste product).

TFF systems can be operated in a recirculation mode, where all or a portion of the retentate is returned to the filter element(s) for further filtration. In a perfusion system, following filtration, the retentate can be returned to a bioreactor where the cell culture media may be maintained for some period of time before being recirculated through the TFF system.

The TFF systems containing filter elements that are employed in recirculating TFF methods can include at least one pump or control valve for recirculating retentate through all or part of the system and at least one conduit for recirculating (e.g., carrying) retentate. The amount of retentate that is recirculated can be controlled using, for example, a pump or a valve. A flow meter can be used to provide a process value for the pump or valve to control the amount of retentate that is recirculated. Thus, in some embodiments, the TFF systems described can further comprise a valve or pump and/or a flow meter for controlling recirculation of retentate. The valve or pump and/or flow meter can be positioned on the retentate outlet or on the flow line carrying retentate out of the system to the retentate receptacle. Alternatively, or in addition, a valve or pump and/or flow meter can be positioned on the peremeate outlet or in the flow line carrying permeate out of the system to control or limit permeate flow.

Maximum achievable flux during TFF system operation can be obtained by selection of an adequate transmembrane pressure (TMP) for permeate discharge. This applies to pressure-dependent and mass-transfer-limited regions of operation. For spiral-wound filters, attainment of the desired TMP is determined by measurement at the end of the module. For cassettes with, for example, two permeate outlets, attainment of the desired TMP is determined by the average feed channel pressure. The transmembrane pressure must be sufficient to support both the pressure drop through the membrane and the maximum pressure to discharge permeate from the permeate channel. Alternatively, or in addition, maximum achievable flux during a TFF system operation can be obtained by selection of an adequate permeate flow rate for permeate discharge. The permeate flow rate can be controlled to a constant value by use of a permeate valve or pump. For perfusion applications, it can be desirable to maintain permeate flow rate at a lower level than would be possible with an uncontrolled permeate stream and to maintain a more stable flow.

TFF systems can also be operated in an alternating flow mode. Alternating flow mode can be achieved by various methods. In a first method, a pump, for example a diaphragm pump, is connected to the retentate port of the filter element. Feed is pulled into the feed port of the filter element by the pump and travels through the feed channel within the filter, out the retentate port, and into the pump. The pump is then reversed and the liquid media (formerly comprising the feed solution) is pushed out of the pump, through the retentate side of the filter element into the feed channel, out the feed port of the filter, and back to the bioreactor. In a second method, a pump alternately pushes and pulls liquid media through the filter element(s). For example, liquid feed is typically introduced to a feed-side of a filter element. The feed is pulled from the bioreactor via a pump (e.g., a pump connected to a feed port of the filter element) and is pushed into the filter element through the feed port. The liquid media then travels through the feed channel, out the retentate port, and back to the bioreactor. The pump then reverses direction, pulling feed from the bioreactor in to the filter element through the retentate port. The liquid media then travels through the feed channel, out the feed port, and through the pump, from which itis then pushed back to the bioreactor. In a third method, a TFF system can be operated in alternating flow mode by use of a pump and a valve block. In this method, the pump continuously pulls a flow of liquid media from the bioreactor and pushes the media into the feed channel of the device. After passing through the pump, valves are used to change a direction of the flow of the liquid media entering the filter. For example, the flow of liquid media initially passes through the pump and enters the feed port of the filter. The media passes through the feed channel and exits the filter through the retentate port, returning to the bioreactor. After a period of time, the valves switch position, causing a flow of liquid media from the pump to enter the retentate port of the filter, pass through the feed channel, and exit the filter through the feed port, then returning to the bioreactor. Alternating flow can create a back flush of the filter membrane to self-clean the membrane and reduce fouling.

The feed pump as illustrated in FIG. 3 can be configured to operate in a recirculation mode and/or an alternating flow mode. The feed pump can be a pump that is not damaging to cells, such as a magnetic levitation pump, a diaphragm pump, a peristaltic pump, or a rotary vane pump. Examples of suitable magnetic levitation pumps include Levitronix® Puralev® Series pump (Levitronix® Technologies, Framingham, MA). Examples of suitable diaphragm pumps include Repligen XCell™ ATF pump (Repligen, Waltham, Mass.). Examples of suitable peristaltic pumps include Watson Marlow Series 500 and Series 600 pumps (Watson Marlow, Wilmington, MA).

Perfusion Processes

In one embodiment, the invention relates to a method of passing a liquid feed through at least one filter element of the invention, separating the liquid feed into permeate and retentate in the filter element; and recovering the permeate and at least a portion of the retentate from the filter element. The liquid feed can comprise a cell culture media, containing cells and a target protein. The target protein can be recovered in the permeate and the cells can be retained in the retentate.

The process can include recirculating at least a portion of the retenate through the filter element(s). Recirculation can be performed on an ongoing basis or at regular intervals to continually harvest product from the cell culture media.

Additionally, recirculating all or a portion of the retentate during start up provides a method by which to ensure that system has reached equilibrium and the retentate has achieved the desired concentration prior to collecting it into the product vessel. It also provides a convenient way to respond to system upsets during processing to provide a more robust process. The fraction of retentate that is recirculated can be adjusted via modulation of the pump or control valve as a way to tune the system in order to assure consistent retentate concentration and/or consistent permeate flow rate to the product collection vessel every run even if cell concentration, new membrane permeability, membrane fouling, membrane permeability, or membrane mass transfer or pressure drop varies from batch to batch. This strategy has particular benefits in the context of continuous processing where the success of subsequent operations rely on the output of a previous operation. Recirculation of retentate can improve cleaning effectiveness through increased cross-flow velocity and reduce cleaning solution through recirculation.

The retentate that is being recirculated can be returned to any upstream location in or before the TFF system (e.g., a bioreactor located upstream of the TFF system). In one embodiment, the retentate is recirculated to the feed tank. In another embodiment, the retentate is recirculated to the feed line near the feed pump before the feed inlet on the TFF system.

In embodiments, the methods described herein comprise performing perfusion (e.g., to remove protein product and cellular waste components from the bioreactor and to supply the liquid feed with fresh media). Perfusion is a type of diafiltration in which continuous bioprocessing occurs. As the perfusion cell culture media undergoes periodic filtration to remove target proteins and waste products, fresh media can be periodically or continuously resupplied. In an embodiment, perfusion is performed by adding the fresh media to the bioreactor at the same rate that permeate is removed from the TFF system, a process which is known in the art as continuous, or constant-volume, perfusion. To perform perfusion or diafiltration, the TFF system can include a reservoir or container for fresh media or diafiltration solution and one or more conduits for carrying fresh media or diafiltration solution from the fresh media or diafiltration solution container to the bioreactor.

In another embodiment, the methods described herein further comprise alternating flow of a liquid through the filter element(s). The method can include reversing a direction of a feed pump, such that liquid feed enters the filter through the retentate-side and exits through the feed-side for a period of time to back flush the membrane. The direction of flow can be reversed, for example, about every twelve seconds or longer.

In yet another embodiment, the invention relates to a perfusion process for harvesting target proteins from a liquid feed containing host cells. The method includes delivering a liquid feed containing target proteins and host cells to a feed channel of at least one filter element of the invention and separating the target proteins from the host cells in the filter element(s). The target proteins can be monoclonal antibodies, which are separated from the host cells by TFF and recovered from the permeate of the filter element(s).

As described above and in Example 4 herein, perfusion processes of the present invention provide several advantages over perfusion processes involving the use of open-channel cassette filter elements and hollow fiber filter elements. Specifically, perfusion processes that include delivering a liquid feed containing host cells to a filter comprising an open microporous membrane and a low-shear feed spacer, provide for increased lifespan of the filter element. As shown, for example, in FIG. 7 and described further with regard to Example 4 herein, higher amounts of target proteins can be recovered from a cell culture solution over longer periods of time using perfusion processes of the present invention over conventional perfusion processes.

In some embodiments, at least about 80%, at least about 90%, or at least about 95% of target proteins can be recovered from a cell culture solution at a harvest throughput of at least about 500 L/m$^2$, at least about 800 L/m$^2$, or at least about 1000 L/m$^2$ of the filter element.

EXEMPLIFICATION

Example 1: Modeling of Feed Spacer Screens

Figure 4A:
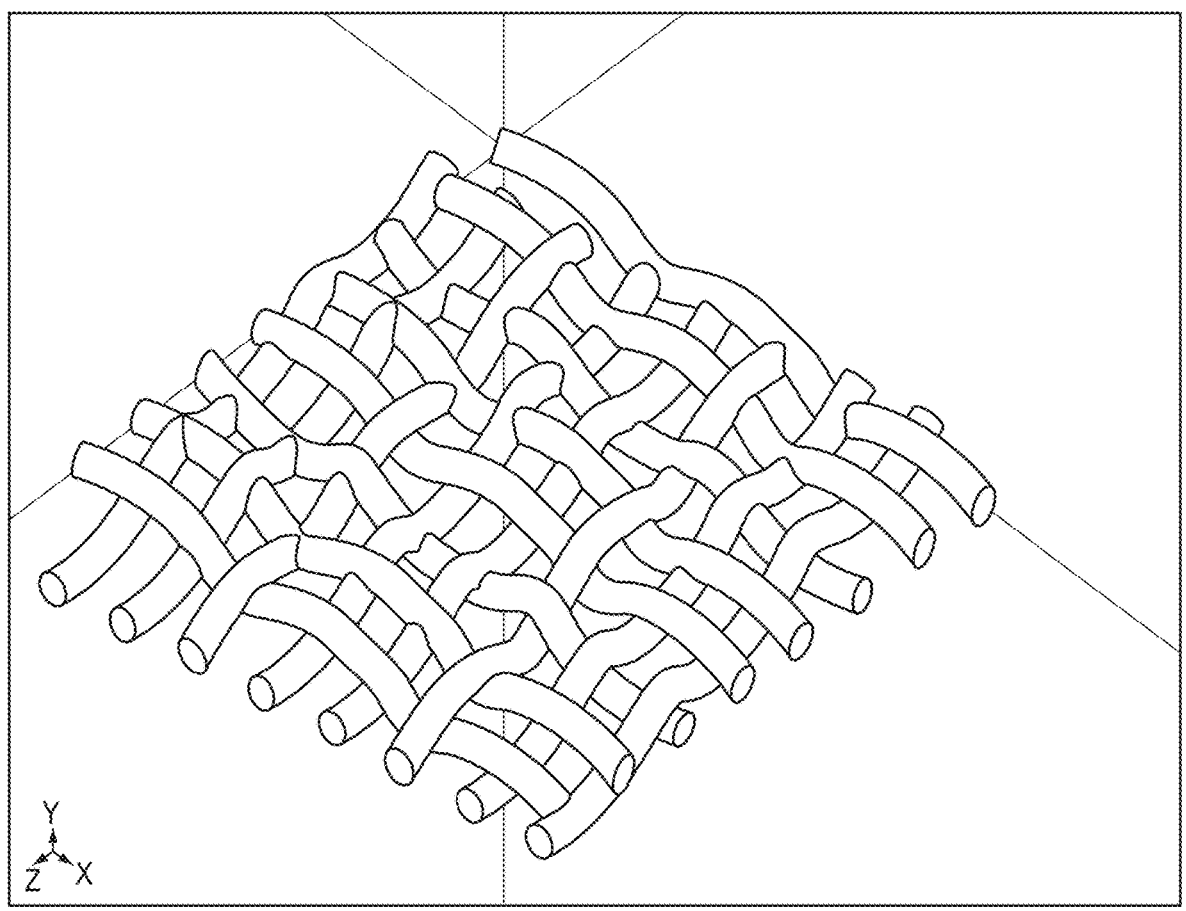
FIG. 4A is a simulated image of a woven-fiber feed spacer.

A modeling study was carried out to evaluate the effects of feed screen parameters on shear rates. The geometry of each of three feed screens was generated for the model using the parametric geometry function in Autodesk Inventor (Autodesk, Inc. Boston, MA). The modeled feed screens included: (1) C-screens (Propyltex® screens, Sefar, QC, Canada) having a two-over-one twill pattern, an open area of 32%, a fiber density of 16.2 fibers/cm, fiber diameter of 270 µm, and a thickness of 515 µm; (2) D-screens (Propyltex® screens, Sefar, QC, Canada) having a two-over-one twill pattern, an open area of 36%, a fiber density of 12.2 fibers/cm, fiber diameter of 340 µm, and a thickness of 610 µm; and (3) D3-screens (Propyltex® screens, Sefar, QC, Canada) having a two-over-one twill pattern, an open area of 39%, a fiber density of 10.6 fibers/cm, fiber diameter of 360 µm, and a thickness of 645 µm. FIG. 4A illustrates a simulation of the D3 woven fiber feed spacer geometry.

Figure 4B:
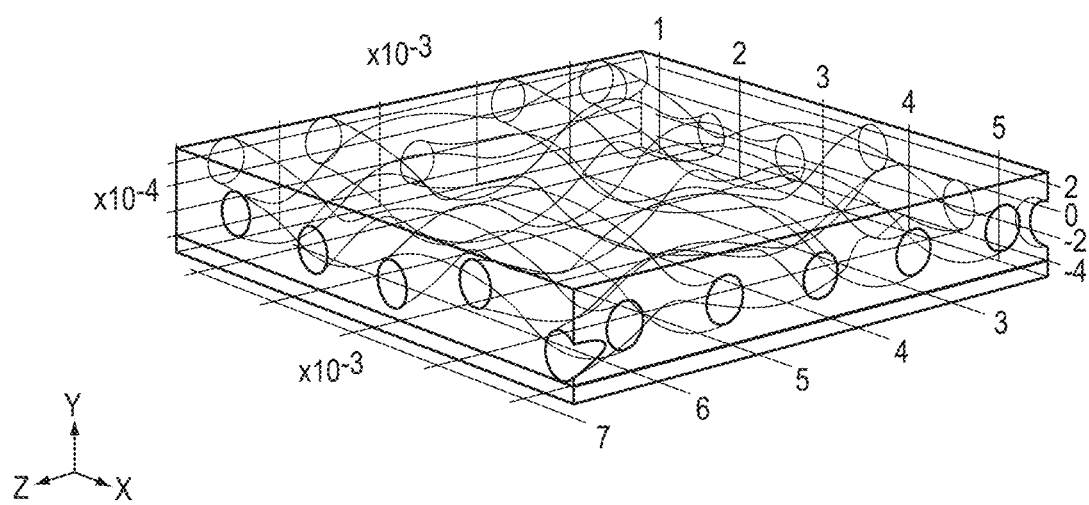
FIG. 4B is a three-dimensional graph of the woven-fiber feed spacer of FIG. 3A.

The feed screen geometries were then imported into COMSOL Multiphysics® Modeling Software (COMSOL, Inc., Burlington MA) to evaluate pressure drop, velocity and shear rates. FIG. 4B illustrates a model of an environment containing the D3 woven fiber feed spacer of FIG. 4A. The model was created using the Particle Tracing Module of the COMSOL software. Boundary conditions for particle travel included a non-permeable upper plate, the geometry of the woven fiber feed spacer and a permeable membrane surface. The membrane properties of the models were based on a MilliporeSigma 0.65 micron Durapore® membrane. The models were created based on the conditions summarized in Table 2.

TABLE 2

| COMSOL model conditions | | | | | | |
|---|---|---|---|---|---|---|
| Feed Flow (ml/min) | Ret Pressure (psi) | Perm Pressure (psi) | Total Membrane Area (cm^2) | Particle Radius (µm) | Particle Density (kg/m^3) | Concentration (num./mil) |
| 50.7 | 3.35 | 3.06 | 74.1 | 5 | 1000-1050 | 2e7 |

Figure 4C:
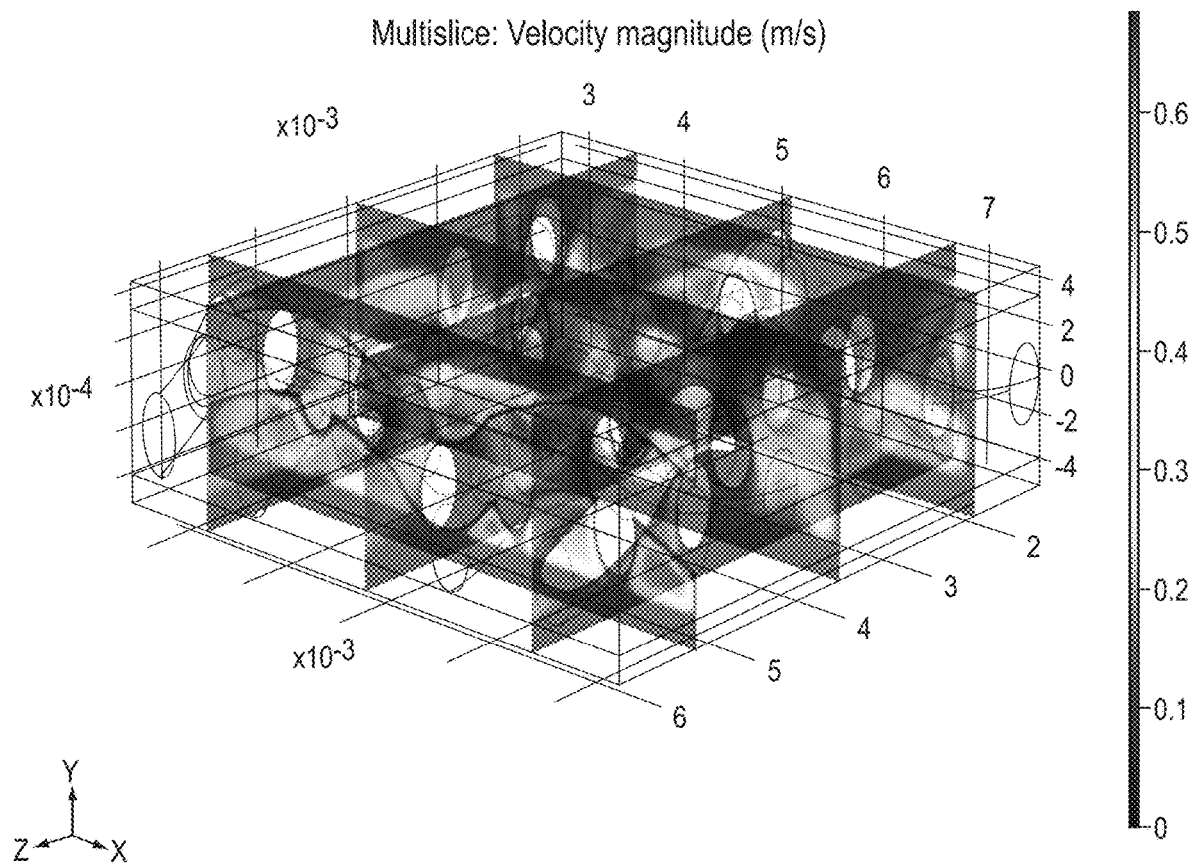
FIG. 4C is a three-dimensional graph of shear modeling results of the woven-fiber feed spacer of FIG. 4A.
Figure 5:
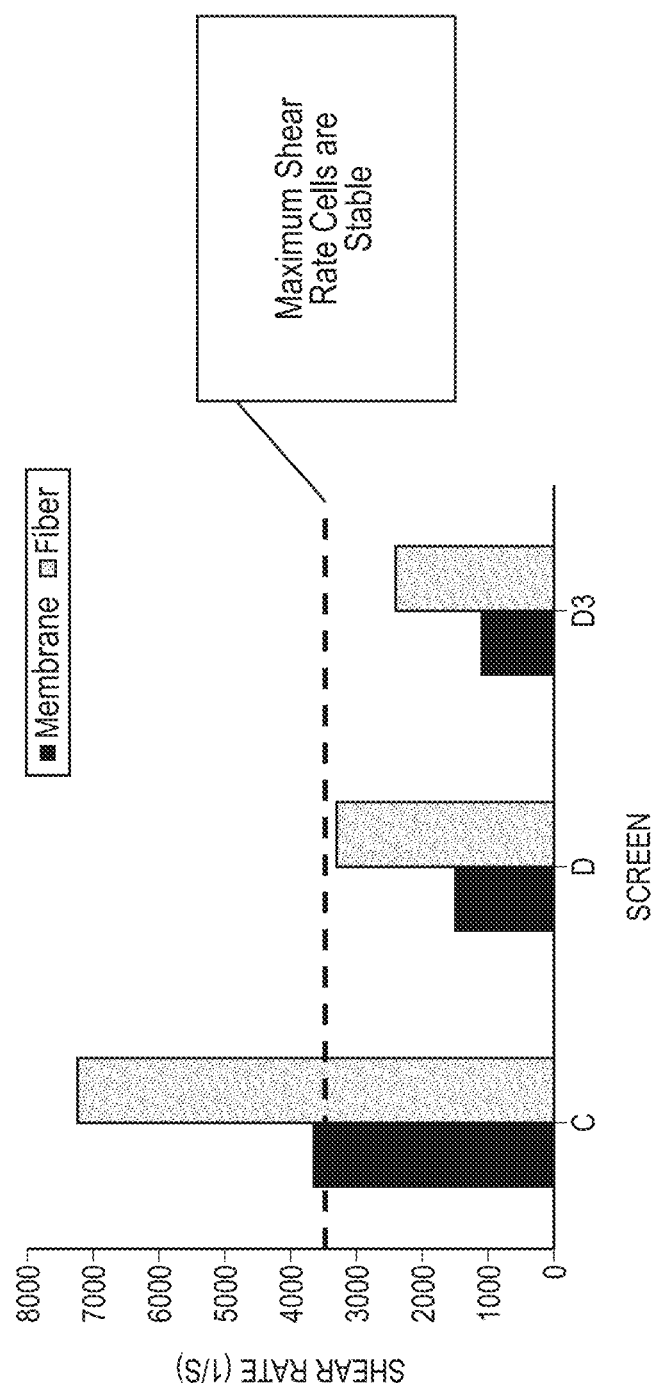
FIG. 5 is a graph of modeled shear rates in an environment having a woven-fiber feed spacer.

FIG. 4C illustrates velocity magnitudes in the model of FIG. 4B with a 6 LMM cross-flow flux in the feed channel. The maximum shear rates at both the membrane and fiber surfaces for each of the screens are shown in FIG. 5. A shear rate of approximately 3500 s$^{-1}$ is the accepted limit for Chinese Hamster Ovarian (CHO) cells, which are the predominant host cell-type used in the production of therapeutic proteins, such as mAbs. As shown in FIG. 5, the shear rates at both the membrane and fiber surfaces of a perfusion filter element sheet containing a C-screen were above the acceptable limit, indicating that CHO cells travelling through a filter element containing such sheets would experience unacceptably high shear. As also shown in FIG. 5, the shear rates of a perfusion filter element containing either a D-screen or a D3-screen were below the acceptable limit.

Example 2: Comparison of Model Results with Experimental Results

Two prototype filter elements were created, each including a single filter element sheet arranged in Pellicon® 3 micro plate and frame format. Both filter element sheets included a 0.65 micron Durapore® membrane. One filter element sheet contained a D-screen feed spacer and the other contained a D3-screen feed spacer. The filter elements underwent testing in an ÄKTAcrossflow™ system (GE Healthcare Lifesciences, Marlborough, MA) with a cell culture solution containing CHO-S cells in a density of 30-60 million cells per milliliter in CHO Cellvento™ 110 media. Feed, retentate and permeate flow were controlled during the experiments and feed pressure measurements were obtained, as shown in FIG. 6. Obtained experimental feed pressures were compared with those of modeled devices using corresponding retentate and permeate pressure values. As shown in FIG. 6, the results of the modeled devices correlated well with feed pressure values as measured with the prototype devices. As such, the model is shown to provide accurate estimates of shear experienced by cells in the feed channels of the prototype devices.

Example 3: Testing of Filter Elements and Pumps

Six different cell retention systems (i.e., perfusion systems) were evaluated, including four systems having commercially available filter elements, and four systems having prototype filter elements. The systems included:
(1) XCell™ ATF-2 system (Repligen, Waltham, MA) with diaphragm pump and a 0.13 m$^2$, 0.2 micron PES hollow fiber filter element. The system was operated in alternating flow mode under recommended cross-flow rates.
(2) XCell™ ATF-2 system with diaphragm pump and a 0.13 m$^2$, 0.5 micron PES hollow fiber filter element. The system was operated in alternating flow mode under recommended cross-flow rates.
(3) Magnetic levitation pump (Levitronix®) and 0.13 m$^2$, 0.5 micron PES hollow fiber filter element. The system was operated in recirculation mode under recommended cross-flow rates.
(4) Peristaltic pump (Watson Marlow) and Prostak™ cassette (MilliporeSigma, Billerica, MA) with 0.06 m$^2$, 0.22 micron PVDF membrane. The system was operated in recirculation mode under recommended cross-flow rates.
(5) Spiral-wound filter element, including a 0.06 m$^2$, 3 micron track-etched membrane (Sterlitech) and D3 feed spacer (Sefar), with peristaltic pump (Watson Marlow). The system was operated in recirculation mode under recommended cross-flow rates.
(6) Spiral-wound filter element, including a 0.06 m$^2$, 3 micron track-etched membrane (Sterlitech) and D3 feed spacer (Sefar), with Levitronix magnetic levitation pump. The system was operated in recirculation mode under recommended cross-flow rates.
(7) Spiral-wound filter element, including a 0.06 m$^2$, 3 micron track-etched membrane (Sterlitech) and D3 feed spacer (Sefar), with Repligen diaphragm pump. The system was operated in alternating flow mode under recommended cross-flow rates.
(8) Spiral-wound filter element, including a 0.06 m$^2$, 5 micron Durapore® membrane (MilliporeSigma) and D3 feed spacer (Sefar), with Repligen diaphragm pump. The system was operated in alternating flow mode under recommended cross-flow rates.

All systems were tested with a feed comprising CHO cells. In particular, MilliporeSigma Mobius® 3 L single use bioreactors were inoculated at 0.5 million cells per milliliter with a CHO-S cell line and CHO Cellvento 110 media. The cells were grown up to 4 million cells per milliliter by day 3, at which point a cell retention system was put online. The perfusion rate in vessel volumes per day was increased from 1 to 3 over days 3-6 and then maintained at 3 for the remainder of the run. Daily cell bleeds started on day 7 to maintain cell densities in the range of 30-60 million cells per milliliter.

The results are shown in FIG. 7. As the membrane area of each of the devices varies, the sieving performance of each of the devices is plotted as a function of device throughput (L/m$^2$, process volume). As shown in FIG. 7, systems (5)-(8) demonstrated significantly improved product sieving as a function of throughput over systems (1)-(4). Additionally, system (8), operating in alternating flow mode, demonstrated the highest percentages of product sieving.

Example 4: Membrane Fouling Testing

Four single-layer filter elements were created with a 0.65 micron Durapore® membrane (MilliporeSigma) in a single layer test cell developed at MilliporeSigma to evaluate different feed channel configurations, including open feed channel and feed channels including various screens. The filter elements underwent testing in an ÄKTAcrossflow™ system to compare feed channel efficiency (open vs. various screens). The system was run utilizing the permeate pump to control TMP. The system was operated in full recirculation mode, sending both the retentate and the permeate back to the feed tank. A crossflow was set for the system and an excursion of flux vs. TMP was performed. Transmembrane pressure values of 1, 2, 3, 4 and 5 psi were targeted for these experiments. The solution was recirculated for 30 minutes at each set TMP and the flux was monitored. The experiment was performed for values where a stable flux was observed. A decreasing flux dictates fouling within the device. All stable flux values are plotted as a function of crossflow and TMP.

The test filter elements included:
(1) Open feed channel (no feed spacer included),
(2) Prostak™ Ultrafiltration (UF) Screen (66% open area, 6.5 fibers/cm fiber density, 326 μm fiber diameter, 590 μm thickness),
(3) D-Screen, and
(4) D3-Screen.

Figure 8A:
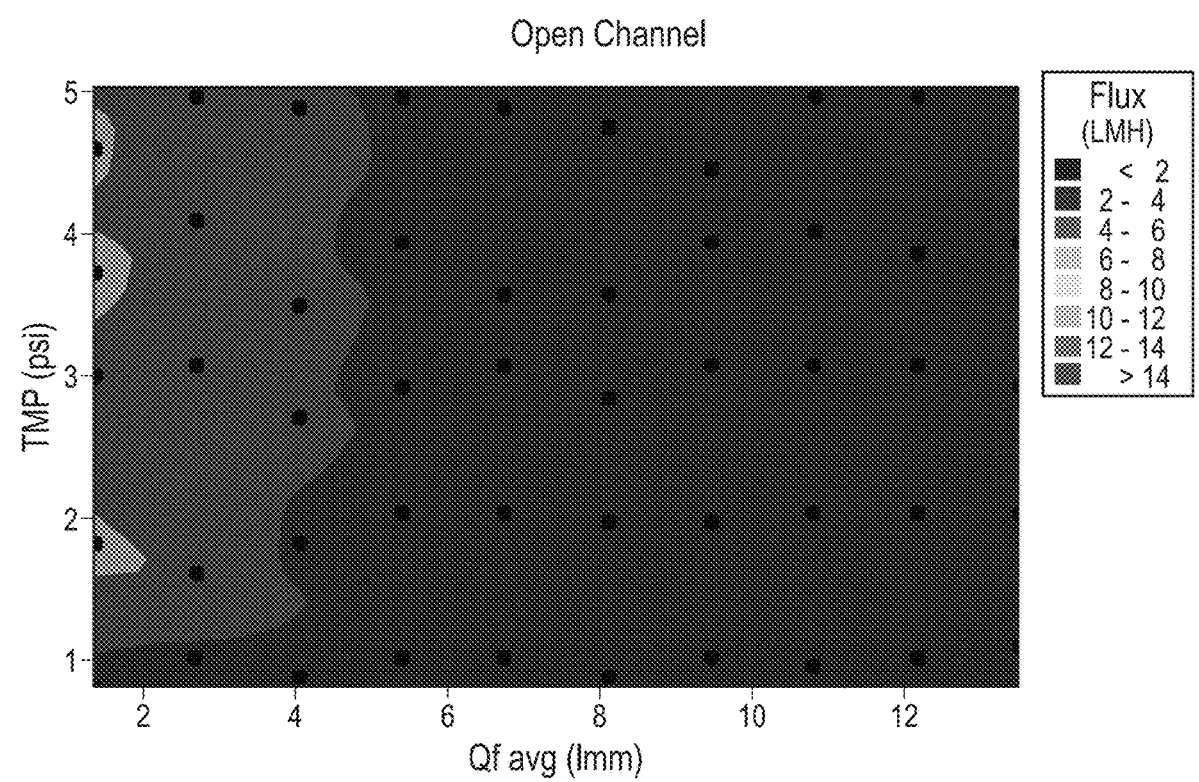
FIG. 8A is a graph of experimental results of membrane fouling in an open-channel filtration device.
Figure 8B:
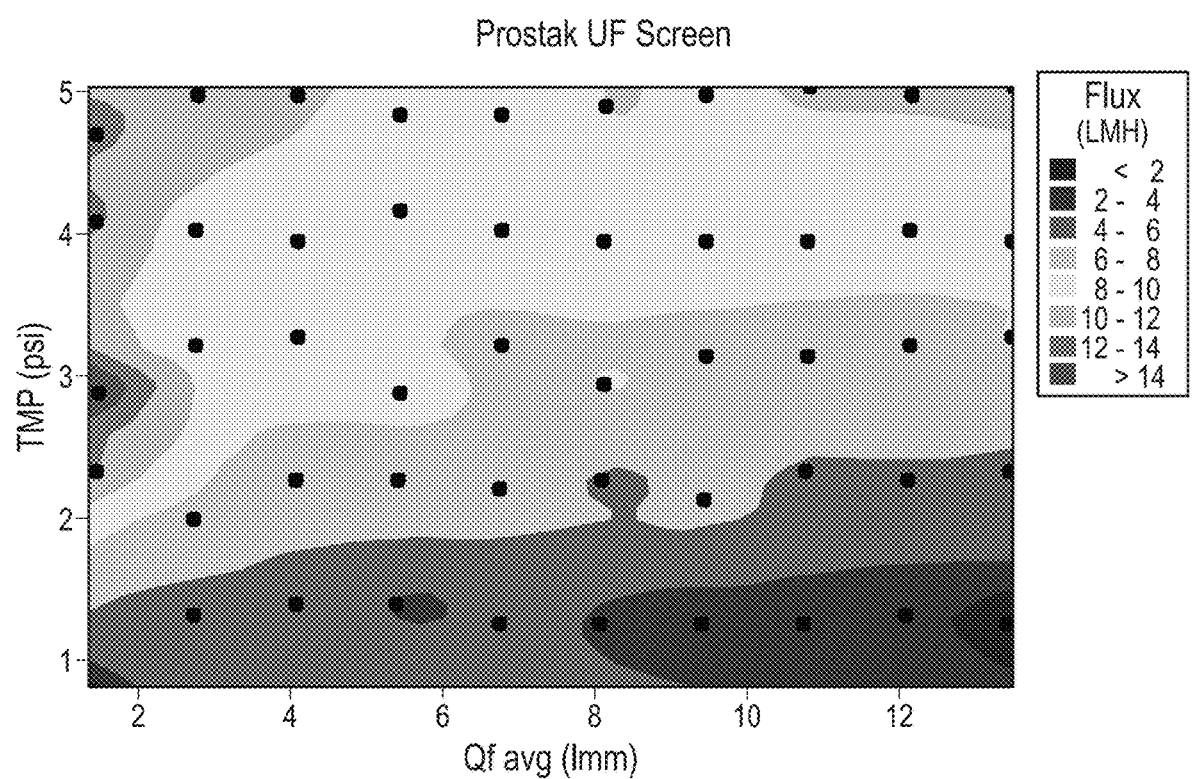
FIG. 8B is a graph of experimental results of membrane fouling in a device with a Prostak™ Ultrafiltration (UF) screen.
Figure 8C:
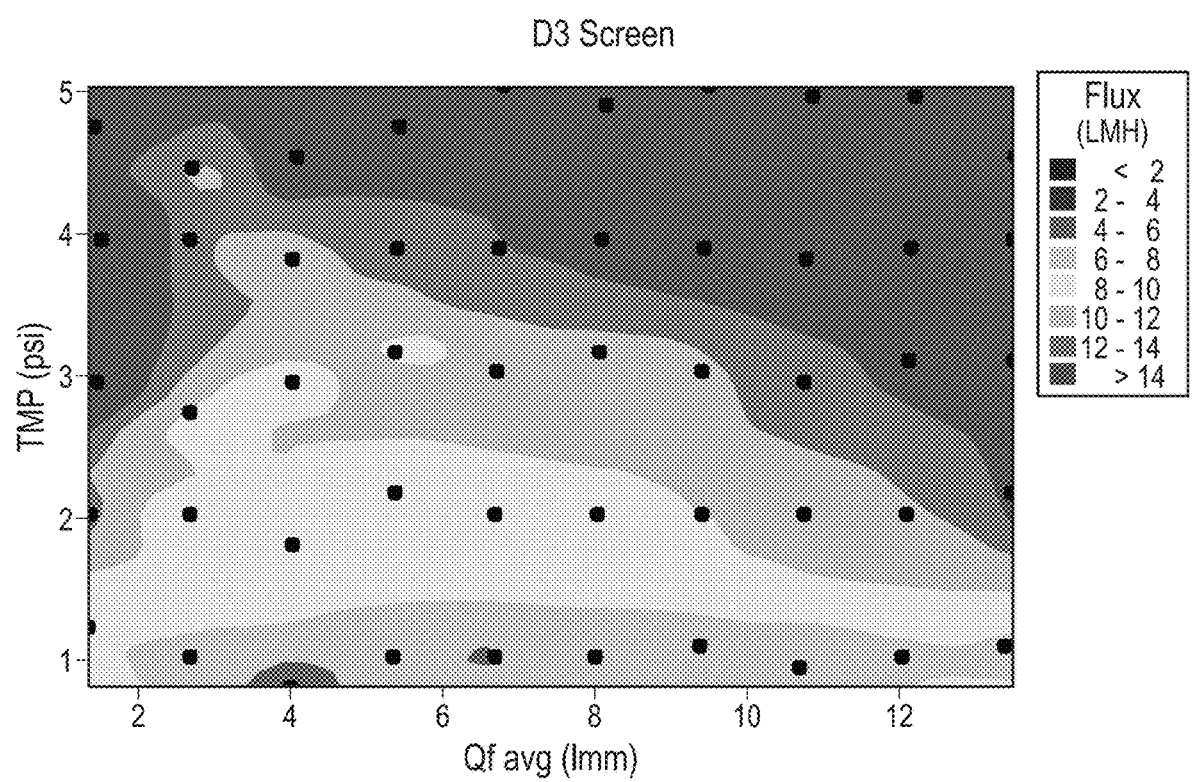
FIG. 8C is a graph of experimental results of membrane fouling in a device with a D3 screen.
Figure 8D:
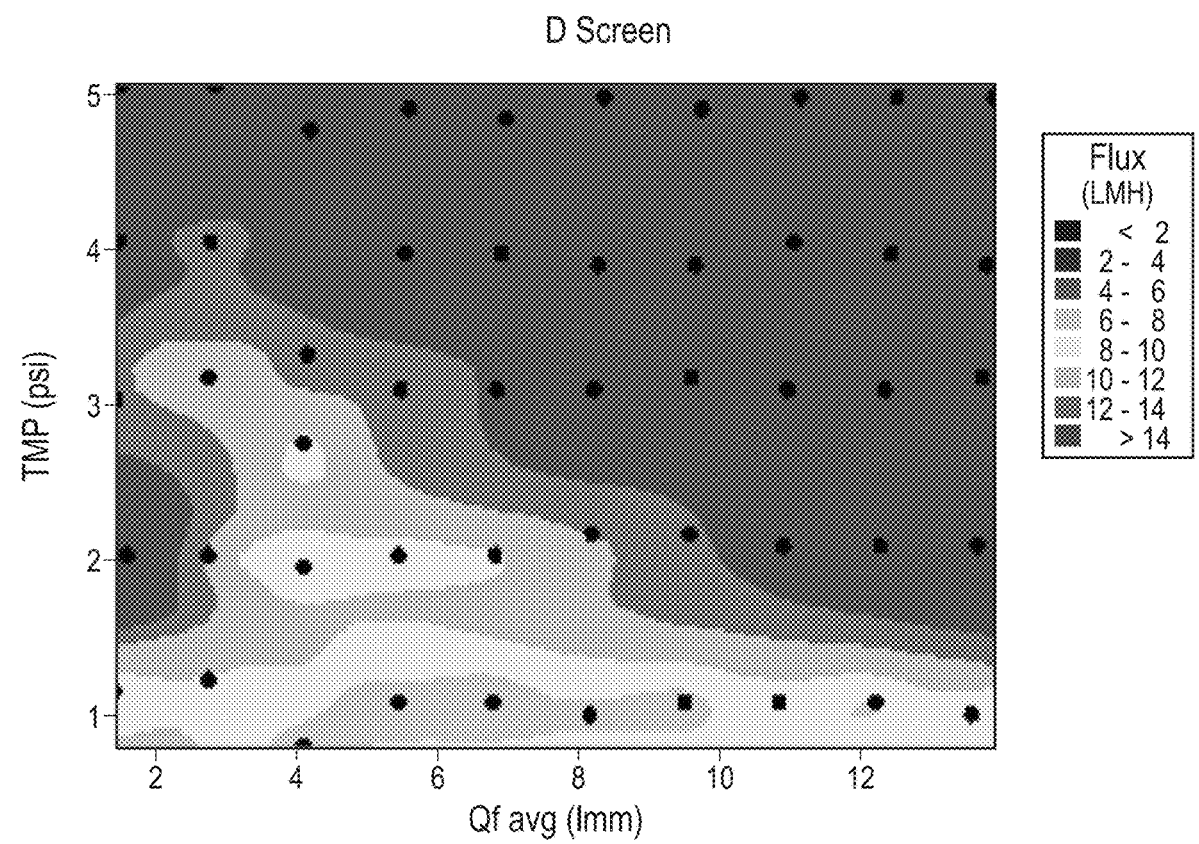
FIG. 8D is a graph of experimental results of membrane fouling in a device with a D screen.

The measured cross-flow fluxes (LMH) of the test filter elements are shown in FIGS. 8A-8D. As shown in FIG. 8A, test filter element (1) demonstrated the lowest flux values across the membrane surface, indicating that the highest amount of membrane fouling occurred in the open-channel device. As shown in FIGS. 8B-8D, filter elements (3) and (4) demonstrated higher flux values than filter element (2), indicating that the D-screen and D3-screen each reduced particle accumulation on the membrane surface to a greater extent than the more tightly woven UF screen.

Example 5: Modeling/Testing of 1 Micron Membranes

Figure 9:
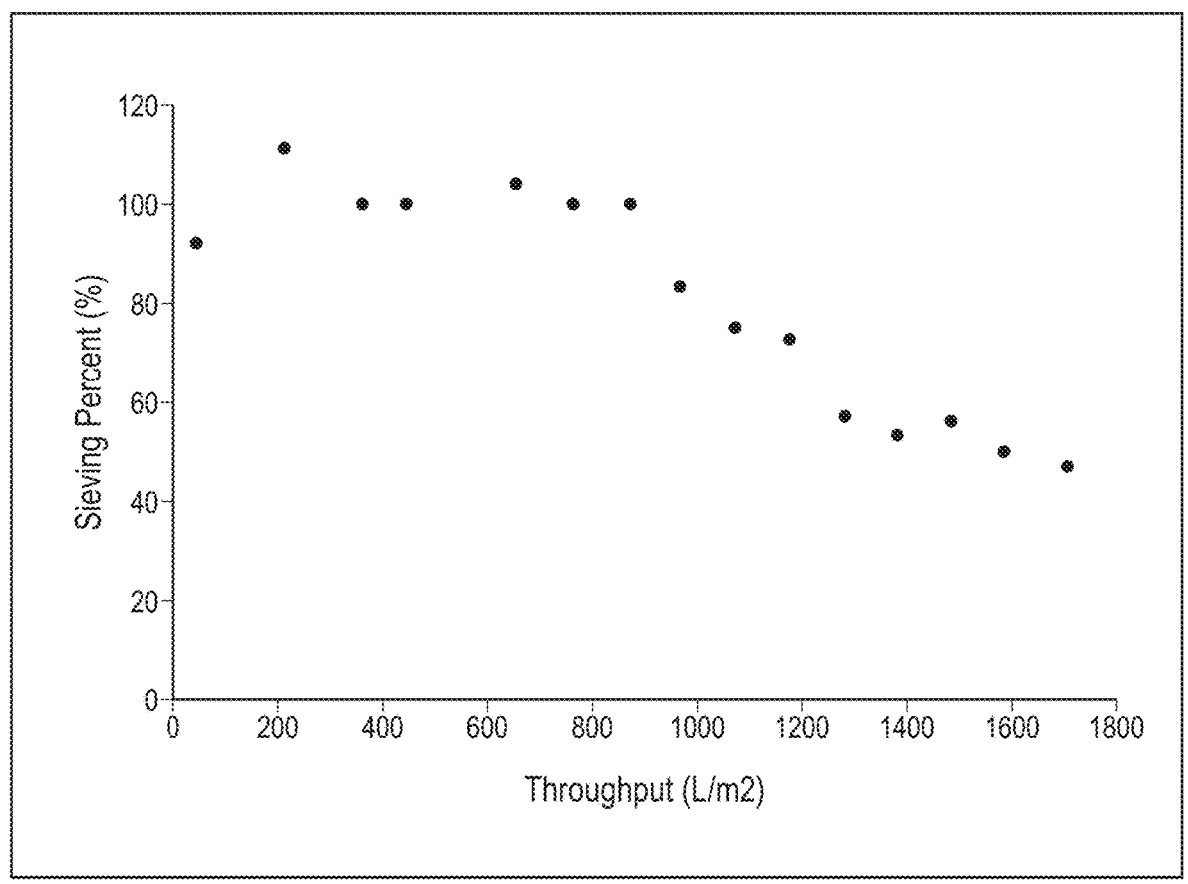
FIG. 9 is a graph of experimental results of sieving versus harvest throughput of a tangential flow filtration device with 1 micron membrane and a D3 screen.

A spiral-wound filter element, including a 0.06 m², 1 micron Durapore® membrane (MilliporeSigma) and D3 feed spacer (Sefar), was tested with a Repligen diaphragm pump. The system was operated in alternating flow mode under recommended cross-flow rates. The system was tested with a feed comprising CHO cells. In particular, MilliporeSigma Mobius® 3 L single use bioreactors were inoculated at 0.5 million cells per milliliter with a CHO-S cell line and CHO Cellvento 110 media. The cells were grown up to 4 million cells per milliliter by day 3, at which point a cell retention system was put online. The perfusion rate in vessel volumes per day was increased from 1 to 3 over days 3-6 and then maintained at 3 for the remainder of the run. Daily cell bleeds started on day 7 to maintain cell densities in the range of 30-60 million cells per milliliter. The results are shown in FIG. 9. As shown in FIG. 9, the 1 micron Durapore® membrane resulted in significantly improved sieving up to a throughput of approximately 900 L/m2.

Example 6: Modeling/Testing of One-Over-One Weave Feed Screens

A spiral-wound filter element, including a 0.06 m², 1 micron Durapore® membrane (MilliporeSigma) and 1 over 1 feed spacer (46% open area, 8.0 n/cm fiber density, 400 μm fiber diameter, 785 μm thickness, Sefar), with Repligen diaphragm pump. The system was operated in alternating flow mode under recommended cross-flow rates. The system was tested with a feed comprising CHO cells. In particular, MilliporeSigma Mobius® 3 L single use bioreactors were inoculated at 0.5 million cells per milliliter with a CHO-S cell line and CHO Cellvento 110 media. The cells were grown up to 4 million cells per milliliter by day 3, at which point a cell retention system was put online. The perfusion rate in vessel volumes per day was increased from 1 to 3 over days 3-6 and then maintained at 3 for the remainder of the run. Daily cell bleeds started on day 7 to maintain cell densities in the range of 30-60 million cells per milliliter.

Figure 10:
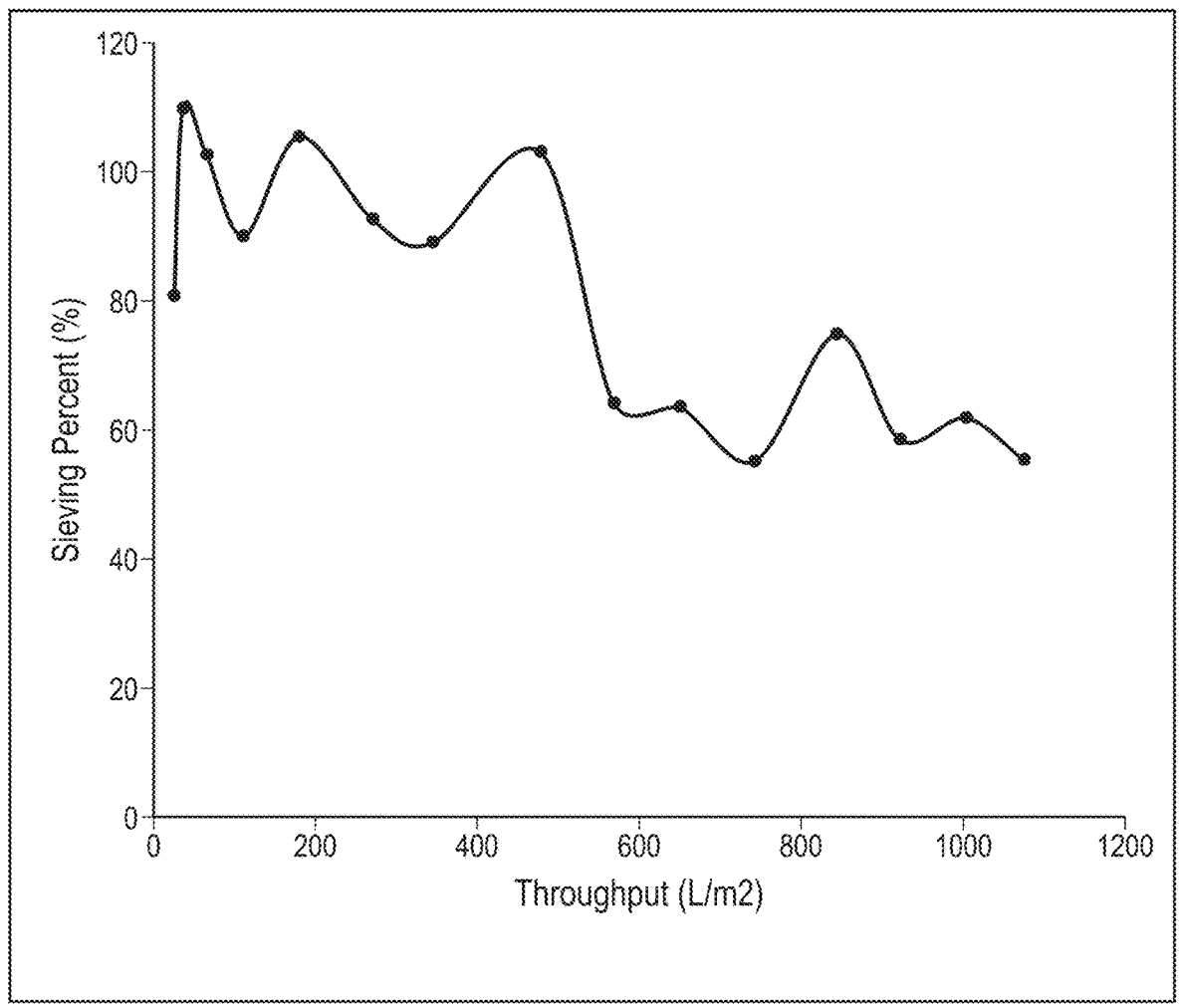
FIG. 10 is a graph of experimental results of sieving versus harvest throughput of a tangential flow filtration device with 1 micron membrane and a one-over-one woven screen.

The results are shown in FIG. 10. As shown in FIG. 10, the one-over-one screen resulted in significantly improved sieving up to a throughput of approximately 500 L/m2.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A perfusion process for harvesting target proteins from a liquid feed comprising the target proteins and host cells, said perfusion process comprising:
    a) providing: i) a perfusion filter element sheet comprising:
       a feed channel having a microporous membrane having a mean pore size of at least about 0.65 μm; and a woven feed spacer comprising woven fibers and having an open area of at least about 35%, the woven fibers having an average fiber diameter of 270 μm to 500 μm and ii) a bioreactor comprising host cells and a target protein;
    b) delivering from the bioreactor the liquid feed comprising target proteins and host cells to a feed channel of at least one perfusion filter element sheet; and
    c) separating the target proteins from the host cells in the at least one perfusion filter element sheet to create a permeate comprising target proteins and a retentate comprising recovered host cells and returning at least a portion of the recovered host cells to the bioreactor.

2. The perfusion process of claim 1, wherein said permeate comprises harvested target proteins.

3. The perfusion process of claim 1, wherein the target proteins are monoclonal antibodies.

4. The perfusion process of claim 1, wherein the host cells are CHO cells.

5. The perfusion process of claim 1, wherein the target proteins are separated from the host cells by tangential flow filtration (TFF).

6. The perfusion process of claim 1, further comprising recovering the target proteins from the at least one filter element.

7. The perfusion process of claim 6, wherein at least about 80% of the target proteins are recovered from the liquid feed at a harvest throughput of at least about 500 L/m² of the filter element.

8. The perfusion process of claim 6, wherein at least about 80% of the target proteins are recovered from the liquid feed at a harvest throughput of at least about 1000 L/m² of the filter element.

9. The perfusion process of claim 6, wherein at least about 90% of the target proteins are recovered from the liquid feed at a harvest throughput of at least about 500 L/m² of the filter element.

10. The perfusion process of claim 6, wherein at least about 90% of the target proteins are recovered from the liquid feed at a harvest throughput of at least about 1000 L/m² of the filter element.

11. The perfusion process of claim 6, wherein at least about 95% of the target proteins are recovered from the liquid feed at a harvest throughput of at least about 500 L/m² of the filter element.

12. The perfusion process of claim 6, wherein at least about 95% of the target proteins are recovered from the liquid feed at a harvest throughput of at least about 1000 L/m² of the filter element.

13. The perfusion process of any one of claim 1, further comprising, supplying a volume of fresh media to the recovered host cells.

14. The perfusion process of claim 1, wherein delivering the liquid feed to the feed channel of the at least one filter element and returning the recovered host cells to the bioreactor occurs on a continuous basis, the recovered host cells being the liquid feed of a subsequent perfusion process.

15. The perfusion process of claim 1, wherein said mean pore size is from about 0.65 μm to about 10.0 μm.

16. The perfusion process of claim 1, wherein said mean pore size is from about 0.65 μm to about 3.0 μm.

17. The perfusion process of claim 1, wherein the open area of said feed spacer is from about 35% to about 55%.

18. The prefusion process of claim 1, wherein the open area of said feed spacer is from about 35% to about 40%.

* * * * *